United States Patent [19]

Eck

[11] 4,301,093
[45] Nov. 17, 1981

[54] ATOMIZER FOR LIQUID

[75] Inventor: Walter Eck, Munich, Fed. Rep. of Germany

[73] Assignee: Bosch Siemens Hausgerate GmbH, Stuttgart, Fed. Rep. of Germany

[21] Appl. No.: 171,425

[22] Filed: Jul. 25, 1980

Related U.S. Application Data

[63] Continuation of Ser. No. 20,707, Mar. 15, 1979, abandoned.

[30] Foreign Application Priority Data

Mar. 15, 1978 [DE] Fed. Rep. of Germany ....... 2811248

[51] Int. Cl.$^3$ .................... B05B 17/06; A61M 11/00
[52] U.S. Cl. .................................. 261/1; 128/200.16; 128/204.13; 239/102; 261/99; 261/104; 261/DIG. 65
[58] Field of Search .............. 261/99, 104, 107, 1, 261/DIG. 65; 128/DIG. 2, 200.16, 204.13; 239/102

[56] References Cited

U.S. PATENT DOCUMENTS

| | | | |
|---|---|---|---|
| 1,916,907 | 7/1933 | Sargent | 261/107 |
| 2,244,792 | 6/1941 | Miller | 261/107 |
| 2,810,561 | 10/1957 | Rosenthal | 261/99 |
| 3,045,450 | 7/1962 | Chandler | 261/99 |
| 3,103,310 | 9/1963 | Lang | 239/102 |
| 3,214,101 | 10/1965 | Perron | 239/102 |
| 3,392,916 | 7/1968 | Engstom et al. | 261/1 |
| 3,633,881 | 1/1972 | Yurdin | 261/DIG. 65 |
| 3,738,574 | 6/1973 | Guntersdorfer et al. | 239/102 |
| 3,970,250 | 7/1976 | Drews | 261/DIG. 65 |
| 4,119,096 | 10/1978 | Drews | 261/DIG. 65 |

FOREIGN PATENT DOCUMENTS 2136456 1/1972 Fed. Rep. of Germany ...... 239/102
2656370 6/1978 Fed. Rep. of Germany ... 128/DIG. 2

Primary Examiner—Gregory N. Clements
Attorney, Agent, or Firm—Herbert L. Lerner

[57] ABSTRACT

Liquid atomizer having a vibration generator for generating vibrations, an atomizer element receiving the vibrations, and a container with liquid to be atomized. Liquid is transported solely and directly from the container to the atomizer element by a wick of elastically resilient material in contact with liquid in the container and at a point remote from the liquid in the container, mechanically coupled to the atomizer element by disposing the wick against the atomizer element. A tube may surround the wick until almost to the coupling point.

8 Claims, 1 Drawing Figure

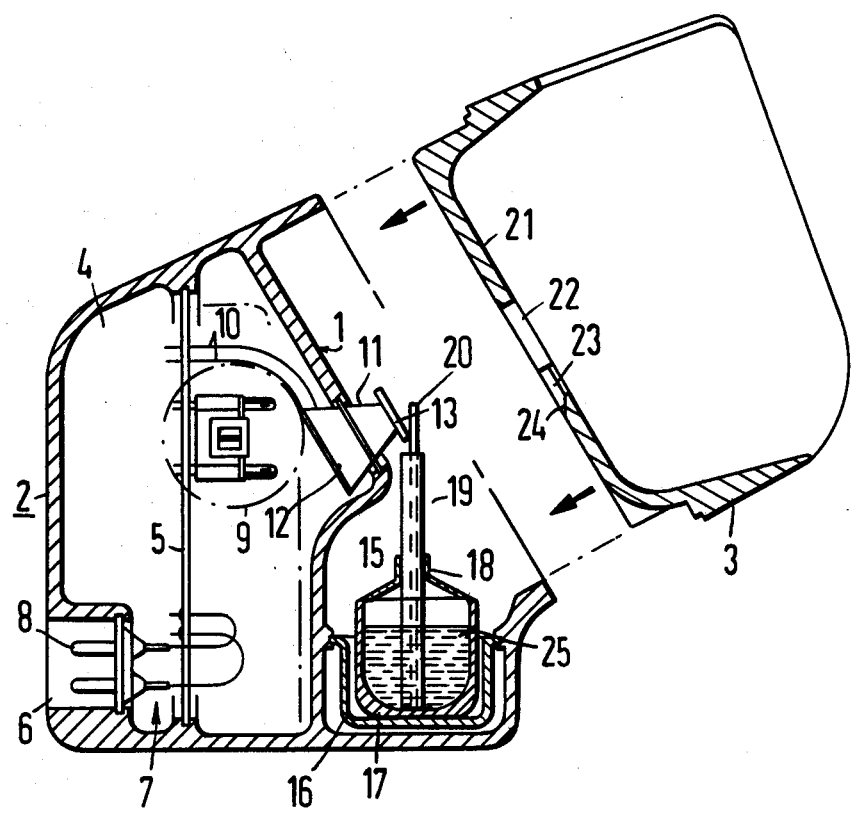

ATOMIZER FOR LIQUID

This is a continuation of application Ser. No. 20,707, filed Mar. 15, 1979, now abandoned.

BACKGROUND OF THE INVENTION

1. Field of the Invention

The invention relates to an atomizer for liquids having a vibration generator preferably generating ultrasonic flexural vibrations, an atomizer element to which the vibrations are transmitted, and a liquid container as well as a liquid feed means arranged between the container and the atomizer element.

2. Description of the Prior Art

In one known liquid atomizer as shown in U.S. Pat. No. 3,103,310, a liquid feed means for the transport of the liquid to be atomized out of the liquid container consists of a distributor element which is rotatable or movable in the manner of a conveyer belt and of a feed wick for the liquid. The wick gives off its liquid to the distributor element outside the zone of the atomizer whereupon the distributor element urges the liquid fed to it into the zone of the vibration generator which then atomizes the liquid. It is a disadvantage here that driving and support devices are necessary for moving the distributor element. Also during extended operation, the wick, which rests against the distributor element in a sliding relationship, is gradually used up whereby an exact transition of the liquid is jeopardized. Not the least of the difficulties which can arise in this known liquid atomizer is that during the feeding motion, the liquid received by the wick accumulates to form major droplets on the distributor element which makes a very fine fog-like atomization questionable.

SUMMARY OF THE INVENTION

It is now an object of the present invention to provide a liquid atomizer of the type mentioned at the outset in which the liquid feed is substantially simplified and the atomization is improved.

With the foregoing and other objects in view there is provided, in accordance with the invention, an atomizer for liquids having a vibration generator for generating vibrations, an atomizer element to which the vibrations are transmitted, a container for holding liquid, liquid feed means arranged between the container and the atomizer element, the improvement includes a wick of elastically resilient material in contact with liquid in the container to cause the liquid to move along the wick, the wick passed to the atomizer element at a point remote from the liquid in the container by disposing the wick against the atomizer element whereby vibrations from the atomizer element are transmitted to the wick and liquid from the wick discharged directly onto the atomizer element, the wick alone feeding liquid from the container directly to the atomizer element.

Other features which are considered as characteristic for the invention are set forth in the appended claims.

Although the invention is illustrated and described herein as embodied in atomizer for liquid, it is nevertheless not intended to be limited to the details shown, since various modifications may be made therein without departing from the spirit of the invention and within the scope and range of equivalents of the claims.

BRIEF DESCRIPTION OF THE DRAWING

The invention, however, together with additional objects and advantages thereof will be best understood from the following description when read in connection with the accompanying drawing which diagrammatically illustrates in section, an atomizer for liquid in accordance with the present invention.

DETAILED DESCRIPTION OF THE INVENTION

In accordance with the invention, a wick consisting of elastically resilient material serves alone for feeding and making available a liquid. The wick is in communication on the one hand with a liquid in a liquid container and on the other hand rests or presses elastically against the atomizer element. Contrary to known liquid atomizers, only a single element is required for feeding and making available a liquid, namely a wick. This not only represents a design simplification but it also ensures that all the liquid taken from the liquid container actually gets to the atomizer element avoiding the formation of larger droplets at the end of the wick. Tests have shown that due to the pressed of the wick to vibrating atomizer element, such as the atomizer plate, the free end of the wick is included in the vibrating systems, i.e. it co-vibrates with a more or less damped vibration amplitude, resulting in a particularly fine fog-like atomization of the liquid.

According to a further development of the invention, a predetermined position and secure pressed of the wick to the atomizer element can be obtained by, until immediately ahead of the coupling point of the wick, running and guiding the wick in a dimensionally very stable wick tube.

According to a further embodiment of the invention, the liquid container which is preferably transparent has an opening which serves as the filling opening as well as the opening for introducing the wick or its wick tube. The wick tube together with the wick, can be taken out of the housing of the liquid atomizer and can be replaced therein too. The opening in the liquid container is preferably so small that no liquid can flow out unintentionally between the rim of the opening and the wick or the wick tube even if the equipment is in inclined position. The liquid atomizer is completely independent of position which means the inhalation equipment can, for instance, also be used in a lying position. It is, in particular, also possible within the scope of the invention to store complete, saleable units consisting of the liquid or a liquid container with atomizer liquid and with the wick inserted.

Such units can be placed in the liquid atomizer, for instance, the inhalation equipment or the room spraying equipment and the like, in a very simple manner.

According to an other embodiment of the invention, good and exact contact of the wick at the atomizer element is ensured by the provision that a spraying head which can be placed on the liquid atomizer and is preferably funnel shaped has a cutout for the atomizer element and for the wick resting against the atomizer element, with a stopping edge which presses the wick or its wick tube and thereby the contained wick against the atomizer element.

Further advantageous details of the invention will be seen from the embodiment example shown in the drawing:

The invention will be illustrated with the aid of an inhalation set for treating the bronchial tract. Spraying head 3 is designed as an inhalation funnel placed, in the direction of the arrows, on the inclined frontside 1 of the equipment housing 2. In the interior 4 of the equipment housing 2 are attached a pluggable circuit board 5 and electrical connecting elements 7 connecting the board 5 to pins 8 which are accessible through a connecting opening 6, as well as a vibration generator 9 for ultrasonic flexural vibrations. Vibration generators are of course known. Vibration generator 9 which is equipped for instance with a low voltage excitation electronic circuit, not further discussed, connected via lines 10 to a conical sound transmitter 11 comprises a piezo-ceramic layer 12 as well as at the end facing the spraying head 3, an atomizer plate 13. The ultrasonic flexural vibrations occurring at the layer 12 are transmitted to the atomizer plate 13. At the lower end of the frontside 1 of the equipment, a cavity 15 is provided. Inside the cavity 15, a trough-like receptacle 16 for a liquid container 17 is arranged. The cavity 15 is covered up against the outside atmosphere by placing the spraying head 3 on it. A liquid container 17 can be placed in the trough-like receptacle 16. Container 17 consists of transparent plastic material which has, at its upper end, a flange opening 18 through which a wick 20 which is in its major part surrounded by a wick tube 19, is introduced into the interior of the liquid container 17. One end of the wick 20 extends to the bottom of the liquid container 17, and on the other end, rests with its other free wick end which protrudes beyond the wick tube 19 against a stop edge 24 or against the plate-like atomizer element 13. The dimensional very stable wick tube 19 holds a wick 20 which consists at least to a large part of elastic material such as a textile fabric which, while flexible, has sufficient rigidity to be self sustaining at least in that section where it elastically presses against the atomizer element. Spraying head 3 which is designed as an inhalation funnel has in its base plate 21 a round opening 22 for insertion of the atomizer plate 13. There is also an elongated opening 23 for the free end of the wick 20 or its wick tube 19 leading into the last mentioned opening. The last mentioned elongated opening 23 has an inclined stopping edge 24 which presses against the wick tube 19 when the spraying head 3 is placed on the equipment housing 2 thereby clamping the free end of the wick 20 elastically relative to the atomizer plate 13, so that contact between the atomizer plate 13 and the wick 20 is ensured. The liquid container 17, the wick tube 19 and wick 20 can be kept in stock as complete saleable units and can be placed in the equipment as required. As soon as the wick 20 comes into contact with the liquid 25, this liquid is transported due to capillary action toward the free end of the wick 20 and is atomized due to the high frequency vibrations of the atomizer plate 13 and therefore also of the end of the wick. This results in the spraying head 3 receiving a very fine distribution of liquid, of for instance particles, having a size of a few thousands of a millimeter per sprayed particle. The liquid 25 is transported without any further action, particularly without additional power consumption, uninterruptedly until the liquid container 17 is empty. The liquid is transported here in accordance with the demand, i.e. in accordance with the atomization of the finely divided liquid.

Any other arrangement and embodiment of the liquid container within the scope of the invention is conceivable, of course. Thus, it is possible to arrange a transparent liquid container in a niche-like recess of the equipment housing in such a manner that, putting the container into place is made even easier and the liquid level can be seen at any time. This is of advantage especially if the liquid atomizer is designed as room spraying equipment or the like; in that case, larger liquid containers which are sufficient for a large number of spraying operations are then used. A switch, for instance, designed as a pushbutton switch may be provided at the periphery of the equipment housing 2, to switch the equipment on or off.

There are claimed:

1. An atomizer for liquids comprising a vibration generator for generating vibrations, an atomizer element to which the vibrations are transmitted, said atomizer element having a surface onto which liquid is fed and from which surface atomized liquid is released, a container for holding a body of liquid below the atomizer element, a housing supporting the vibration generator, the atomizer element, and the container, a rod-shaped wick of elastically resilient material in contact with the body of liquid in the container to cause the liquid to move upwardly along the wick, means for elastically pressing the wick against said surface at a point remote from the body of liquid in the container to cause liquid from the wick to discharge directly onto said surface, said wick alone feeding liquid from the container directly to the atomizer element.

2. Liquid atomizer according to claim 1, wherein the wick is run and guided in a dimensionally stable wick tube from the container until immediately before its contact point with the atomizer element.

3. Liquid atomizer according to claim 2, wherein the atomizer element is an atomizer plate, and wherein the wick presses elastically against the atomizer plate with point or line contact.

4. Liquid atomizer according to claim 2, said means being a stopping edge disposed against the wick to cause the wick to press elastically against the atomizer plate.

5. Liquid atomizer according to claim 1, wherein the atomizer element is an atomizer plate, and wherein the wick presses elastically against the atomizer plate with point or line contact.

6. Liquid atomizer according to claim 5, said means being a stopping edge disposed against the wick to cause the wick to press elastically against the atomizer plate.

7. Liquid atomizer according to claim 1, wherein the container is transparent to permit sight of liquid therein, and wherein the container has an opening which serves as a filling opening for the liquid as well as for introducing the wick together with its wick tube, if any, into the container, and wherein the container with the liquid and wick can be taken and replaced into the housing of the liquid container.

8. An atomizer for liquids comprising a vibration generator for generating vibrations, an atomizer element to which the vibrations are transmitted, said atomizer element having a surface onto which liquid is fed and from which surface atomized liquid is released, a container for holding a body of liquid below the atomizer element, a housing supporting the vibration generator, the atomizer element, and the container, a rod-shaped wick of elastically resilient material in contact with the body of liquid in the container to cause the liquid to move upwardly along the wick, means for elastically pressing the wick against said surface at a point remote from the body of liquid in the container to cause liquid from the wick to discharge directly onto said surface, said wick alone feeding liquid from the container directly to the atomizer element and, wherein a spraying head is adapted to be placed on the housing of the liquid atomizer, said spraying head having a base plate with a cutout aligned for the atomizer element to spray liquid into the spraying head, and another second cutout for the wick disposed against the atomizer element, and a stopping edge on the baseplate impeding movement in said second cutout which causes the wick to press against the atomizer element.

* * *